United States Patent [19]
Hohberg et al.

[11] Patent Number: 5,164,586
[45] Date of Patent: Nov. 17, 1992

[54] ARRANGEMENT FOR MEASURING THE ABSORPTION OF TRANSPARENT SPECIMENS MOUNTED WITHIN AN INTEGRATING SPHERE

[75] Inventors: Gerhard Hohberg, Aalen; Axel Matthes, Königsbronn; Harry Schlemmer, Oberkoechen, all of Fed. Rep. of Germany

[73] Assignee: Carl-Zeiss-Stiftung, Heidenheim

[21] Appl. No.: 704,177

[22] Filed: May 22, 1991

[30] Foreign Application Priority Data

May 23, 1990 [DE] Fed. Rep. of Germany ... 9005845[U]

[51] Int. Cl.$^5$ ................................................ H01J 5/16
[52] U.S. Cl. .................................. 250/226; 250/228; 356/236; 356/328; 356/319
[58] Field of Search .............. 250/228, 226; 356/236, 356/328, 319, 326

[56] References Cited

U.S. PATENT DOCUMENTS

| | | |
|---|---|---|
| 3,944,368 | 3/1976 | Beesley . |
| 4,093,991 | 6/1978 | Christie, Jr. et al. . |
| 4,120,582 | 10/1978 | De Vries et al. ............... 356/236 |
| 4,232,971 | 11/1980 | Suga ........................... 250/228 |
| 4,259,011 | 3/1981 | Crumm et al. . |
| 4,598,715 | 7/1986 | Mächler et al. . |
| 4,802,763 | 2/1989 | Gerlinger et al. ............. 356/319 |
| 4,892,409 | 1/1990 | Smith .......................... 356/236 |
| 4,900,923 | 2/1990 | Gerlinger . |
| 4,965,454 | 10/1990 | Yamauchi et al. . |

FOREIGN PATENT DOCUMENTS

| | | |
|---|---|---|
| 0412168 | 2/1991 | European Pat. Off. . |
| 2340546 | 9/1977 | France . |
| 56-122936 | 9/1981 | Japan . |
| 2010474 | 6/1979 | United Kingdom . |
| 2110416 | 6/1983 | United Kingdom . |

OTHER PUBLICATIONS

Article by E. Wendland entitled "Messung der diffusen Reflection mit der Ulbricht-Kugel" published in GIT Fachz. Lab., vol. 9, 1988, pp. 993 to 997.

*Primary Examiner*—David C. Nelms
*Assistant Examiner*—Que T. Le
*Attorney, Agent, or Firm*—Walter Ottesen

[57] ABSTRACT

The invention is directed to an arrangement for measuring the absorption of a transparent specimen. The arrangement includes: a radiation source for supplying radiation; a radiation-integrating device defining a space enclosed by a wall having a reflective surface for multiply reflecting the radiation substantially uniformly throughout the space to diffusely illuminate the transparent specimen whereby diffused radiation passes through the transparent specimen; a photometric measuring unit for measuring the radiation passed through the specimen; and, a mount for mounting the specimen between the reflective surface and the measuring unit. The arrangement of the invention enables the absorption of transparent specimens to be measured which have unfavorable outer forms such as where the specimen contains no surfaces which are mutually parallel.

14 Claims, 3 Drawing Sheets

ARRANGEMENT FOR MEASURING THE ABSORPTION OF TRANSPARENT SPECIMENS MOUNTED WITHIN AN INTEGRATING SPHERE

Field of the Invention

The invention relates to an arrangement for measuring the absorption of transparent specimens. The arrangement includes a radiation source, a radiation-integrating device and a photometric measuring unit.

BACKGROUND OF THE INVENTION

Conventional photometers are poorly suited for measuring the absorption of transparent specimens which have a nonuniform or complicated outer form. It is known to utilize photometers equipped with an Ulbricht sphere for specimens which have an outer form suitable for photometric measurements but which scatter greatly.

An arrangement of this kind is described for example in an article by E. Wendland entitled "Messung der diffusen Reflexion mit der Ulbricht-Kugel" and published in GIT Fachz. Lab., Volume 9, 1988, pages 993 to 997. The arrangement includes a conventional single-beam spectral photometer having an accessory in the form of an integrating sphere which is generally known as an Ulbricht sphere. The inner surface of the Ulbricht sphere has a good reflectivity and reflects radiation incident thereon without a preferred direction. The Ulbricht sphere has two openings for measurements on transparent specimens. The specimen is mounted ahead of one opening and irradiated with monochromatic light which impinges virtually vertically on the specimen. The radiation leaves the specimen in a large angular range in the sphere because of the diffusion. This radiation is reflected so often from the good reflecting inner surface of the Ulbricht sphere until the radiation passes through the second opening of the sphere and impinges on a detector behind the sphere.

This known arrangement has the disadvantage that it is poorly suited or not at all suited for solid specimens such as cut diamonds and other precious stones which do not have two mutually parallel surfaces. Many other solid transparent specimens whose absorption or spectral absorption one wishes to measure do not have two surfaces which are at least approximately parallel to each other without processing and which are suitable for optical measurements.

SUMMARY OF THE INVENTION

It is an object of the invention to provide an arrangement with which the absorption of transparent specimens having unfavorable outer forms can be measured as well as possible.

The arrangement of the invention is for measuring the absorption of a transparent specimen and the arrangement includes: a radiation source for supplying radiation; a radiation-integrating device defining a space enclosed by a wall having a reflective surface for multiply reflecting the radiation substantially uniformly throughout the space to diffusely illuminate the transparent specimen whereby diffused radiation passes through the transparent specimen; photometric measuring means for measuring the radiation passed through the specimen; and, mounting means for mounting the specimen between the reflective surface and the measuring means.

In an advantageous embodiment of the invention, a smooth face of the specimen is positioned toward the photometric measuring unit. It is especially advantageous to provide a glass plate as the supporting surface for the specimen through which the radiation passed by the specimen reaches the photometric measuring unit. If the specimen has no smooth face, then it is especially advantageous to introduce a liquid between the specimen and the glass plate which is absorption free in the spectral range of interest.

In a further advantageous embodiment, a light conductor is mounted between the specimen and the photometric measuring unit. The light conductor receives a portion of the radiation which has passed through the specimen. It is especially advantageous to utilize a diode-array spectrometer as a photometric measuring unit.

In another embodiment of the invention, the photometric measuring unit comprises at least one filter and a photoelectric detector. The filter and photoelectric detector can be mounted at a distance from the specimen by using a lens or a light conductor.

A further embodiment of the invention provides that the photometric measuring unit contains a reference device.

The radiation source can be mounted in the radiation-integrating device and it is then especially advantageous to utilize a flash lamp.

The radiation source can also be coupled to the radiation-integrating device via an imaging optic.

For many specimens it is advantageous to configure the supporting surface on the glass plate as a diffusing screen.

It is especially advantageous to utilize an Ulbricht sphere as the radiation-integrating device. However, other embodiments are possible such as a cylindrically-shaped housing having inner surfaces provided with a good and diffusing reflective coating.

For large specimens, the specimen can be arranged in a cylindrically-shaped tube which has a reflecting inner surface and is seated on the radiation-integrating device.

BRIEF DESCRIPTION OF THE DRAWINGS

The invention will now be described with reference to the drawings wherein.

DESCRIPTION OF THE PREFERRED EMBODIMENTS OF THE INVENTION

Figure 1:
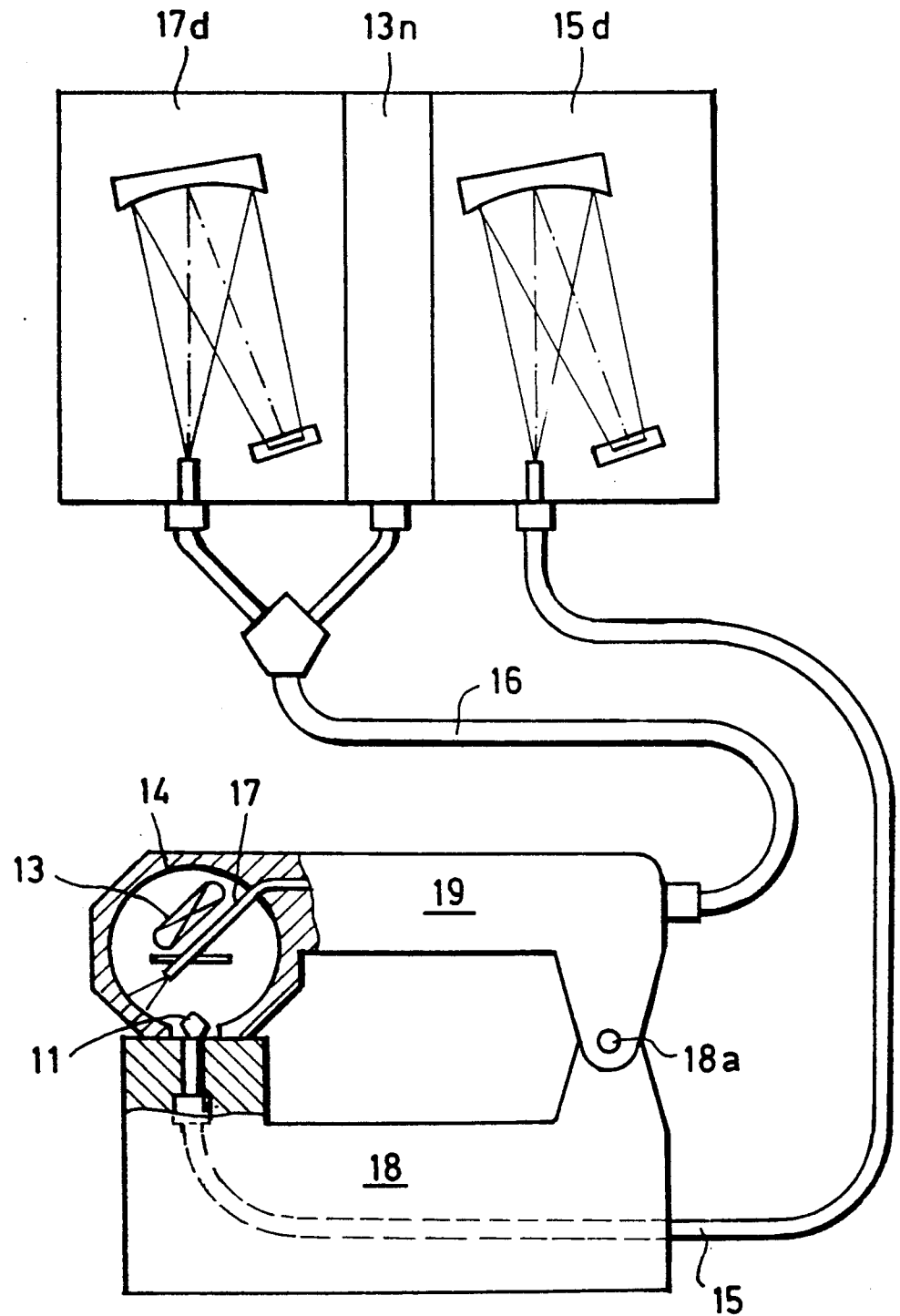
FIG. 1 is an arrangement for measuring the spectral absorption.
Figure 2:
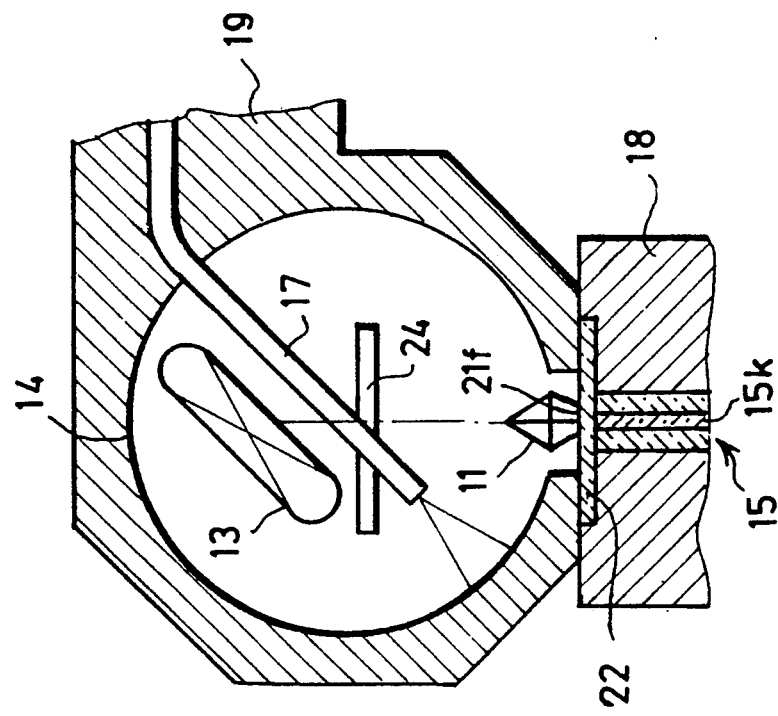
FIG. 2 is an enlarged view of the measuring head of the arrangement shown in FIG. 1.

In FIG. 1, reference numeral 11 identifies a specimen which is shown enlarged together with the measuring head of the arrangement in FIG. 2. The specimen 11, for example a precious stone, sits with a face 21f on a glass plate 22 having a supporting surface which can be configured as a diffusing screen. The face 21f is as large as possible and smooth or is a distinguished face. The face 21f is a crystallographically important face, one which is important to the function of the specimen or the like. The specimen 11 is diffusely illuminated by a flash lamp 13 via the Ulbricht sphere 14. A direct illumination is prevented by the baffle 24 which has a good and diffusely reflecting surface in the same manner as the Ulbricht sphere 14.

The radiation which has passed through the specimen 11 is received by the core 15k of the light conductor 15. The core conducts the radiation to the inlet slit of the diode-array spectrometer 15d which determines the spectral variation of the radiation passed through the specimen 11 and directs the radiation to an evaluation unit (not shown).

A flash lamp such as Type BGG 1015 Z1 of the Heimann Company is suitable as a radiation source. The Heimann Company is a firm organized and doing business in the Federal Republic of Germany. The flash lamp is supplied with the necessary voltage via the cable 16 from the power supply unit 13n. The radiation distribution is subjected to fluctuations from flash to flash so that it is appropriate in this embodiment to make a reference measurement simultaneously with the measurement of the specimen 11. For this purpose, the reflected radiation is detected from a region of the Ulbricht sphere 14 by the light conductor 17 with this region likewise not being illuminated directly by the flash lamp 13. This radiation is supplied to a second diode-array photometer 17d with the measuring values thereof likewise being transmitted to the evaluation unit which evaluates the measured values in a known manner.

A diode-array spectrometer of the type identified by reference numerals 15d and 17d is disclosed, for example, in U.S. Pat. No. 4,598,715.

In an advantageous embodiment of the invention, the glass plate 22 is an element of a lower apparatus component 18 having a pivot bearing 18a defining a pivot axis. The upper part 19 with the Ulbricht sphere 14 can be pivoted about this pivot axis whereby making the supporting surface of the glass plate 22 accessible.

Figure 3:
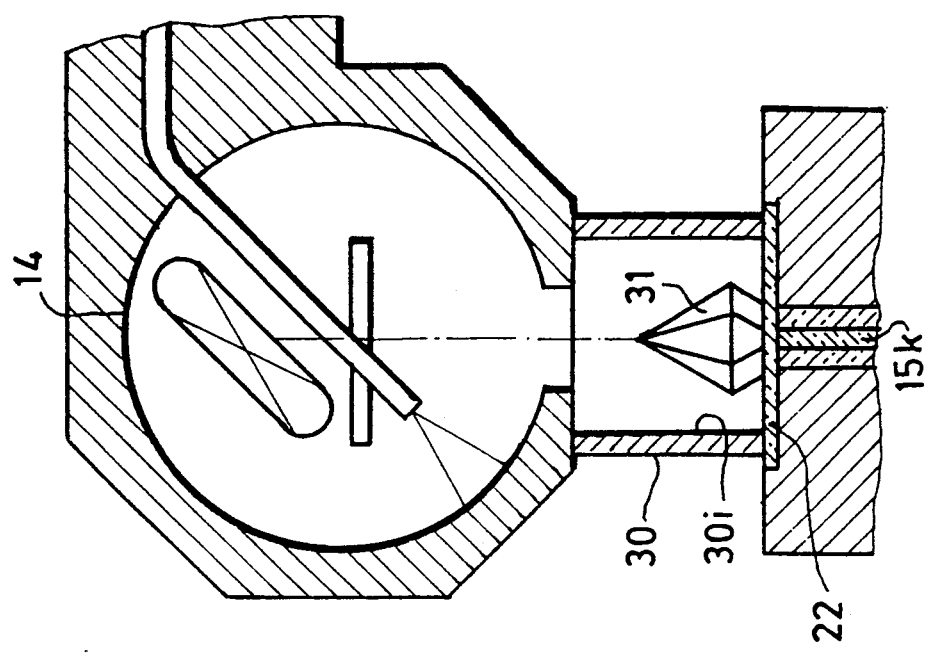
FIG. 3 is an accessory for the measuring head for measuring large specimens.

FIG. 3 shows an accessory for the above-described arrangement by means of which it is possible to measure a specimen 31 which is too large for the arrangement shown in FIG. 2. For this purpose, a cylindrically-shaped tube section 30 is used which has a good reflecting inner surface 30i. Such an accessory is disclosed in U.S. Pat. No. 4,900,923 for making measurements with an Ulbricht sphere on reflecting specimens.

Figure 4:
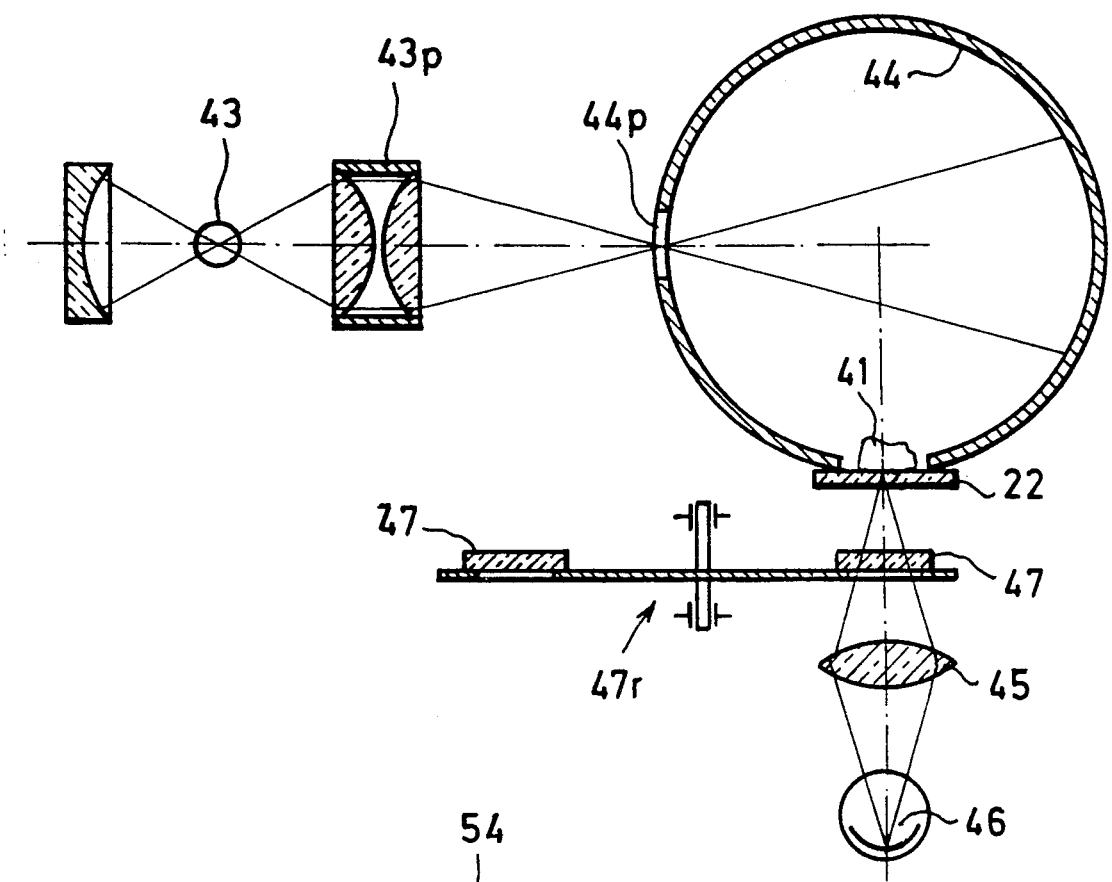
FIG. 4 is an arrangement for measuring the absorption at one or a few wavelengths; and, FIG. 5 is a cylindrically-shaped radiation-integrating device.

FIG. 4 shows an example for the measurement at one or several wavelengths with a unit for simultaneous reference measurement being dispensed with. For this reason, a radiation source 43 is used which is driven with the same radiation power until a reference measurement without specimen or with a standard and at least one specimen is measured. The radiation source 43 can, for example, be a halogen lamp or a spectral lamp. The radiation source is imaged via the objective 43p into the opening 44p of the Ulbricht sphere 44 and illuminates the specimen 41 without a preferred direction as a consequence of the multiple reflections of the radiation within the sphere.

The specimen sits with a smooth surface on the glass plate 22 having a supporting surface configured as a diffusing screen. The supporting surface of the glass plate 22 is imaged by the lens 45 on the photoelectric detector 46. Measurement and evaluation take place in a manner known for single-beam photometers. Either one filter or several filters 47 in a filter wheel 47r are mounted between specimen 41 and the detector 46.

It is also possible to mount the filter and receiver close behind the specimen without using a lens.

In FIG. 4, the specimen 41 shown is not a precious stone but is instead a specimen which has only one smooth face which is used as a supporting face. Even specimens of this kind can be used with all embodiments described herein and the measurement results thereof provide in many cases adequate and important data. In case the specimen does not have an adequately smooth face, it is also possible to seat the specimen on the supporting surface with a suitable liquid which is not absorbent in the spectral range of interest. Such a liquid can be, for example, toluine or commercially available immersion oils.

Figure 5:
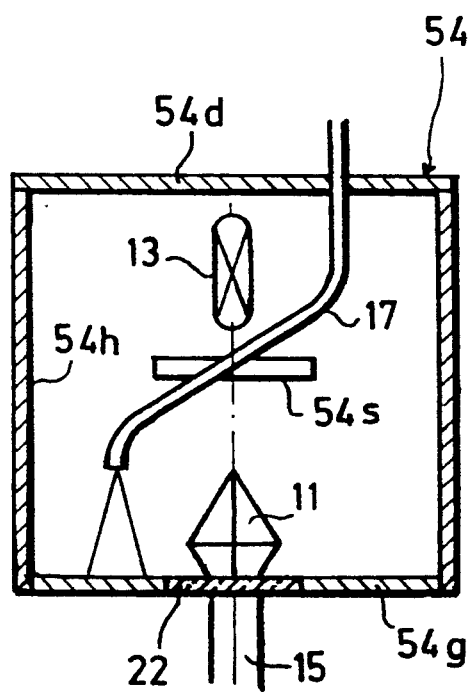

The Ulbricht sphere is well known as a unit for providing multiple reflections without a preferred direction for the diffuse illumination of a specimen. For many applications, other embodiments of the invention are possible depending upon the metrological requirements and these embodiments are more cost-effective to produce than a sphere. An example of such an embodiment is provided in FIG. 5. The radiation-integrating device 54 comprises a cylindrical section 54h, base plate 54g and a cover plate 54d with all inner surfaces being coated with a good and diffusing reflective coating. As in FIGS. 1 and 2, reference numeral 11 identifies the specimen, 22 the glass plate, 15 the light conductor for the measurement radiation and 17 the light conductor for the reference radiation. Reference numeral 54s identifies a baffle configured in correspondence to the conditions present in the device 54.

The individual components of the arrangements described herein can be combined in many ways. Accordingly, it is, for example, possible to equip the photometric measuring unit shown in FIG. 4 with filters and with a reference device. On the other hand, the flash lamp 13 in FIG. 1 can be substituted by the illumination device of FIG. 4.

It is understood that the foregoing description is that of the preferred embodiments of the invention and that various changes and modifications may be made thereto without departing from the spirit and scope of the invention as defined in the appended claims.

What is claimed is:

1. Arrangement for measuring the absorption of a transparent specimen, the arrangement comprising:
   a radiation source for supplying broad band light radiation;
   a radiation-integrating device defining a space enclosed by a wall having a reflective surface for multiply reflecting said radiation substantially uniformly throughout said space to diffusely illuminate the transparent specimen exclusively by diffusely reflected radiation whereby diffused radiation passes through the transparent specimen;
   a diode array spectrometer for measuring the radiation passed through the specimen; and,
   mounting means for mounting the specimen within said space and between said reflective surface and said diode array spectrometer.

2. The arrangement of claim 1, the specimen having a smooth face and said mounting means defining a surface for holding the specimen so as to cause the smooth face of said specimen to be directed toward said diode array spectrometer.

3. The arrangement of claim 1, said mounting means being a glass plate defining a supporting surface for supporting the specimen thereon.

4. The arrangement of claim 3, wherein said measuring means measures the radiation passed through the specimen in a predetermined spectral range, the arrangement further comprising a liquid interposed between the specimen and said glass plate, said liquid being nonabsorptive in said spectral range.

5. The arrangement of claim 1, further comprising a light conductor disposed between the specimen and said diode array spectrometer for conducting the radiation form the specimen to said diode array spectrometer.

6. The arrangement of claim 1, including a photometric measuring reference unit for measuring the radiation reflected from the reflective surface.

7. The arrangement of claim 1, said radiation source being mounted within said space.

8. The arrangement of claim 1, said radiation source being a flash lamp.

9. The arrangement of claim 1, said radiation source being disposed outside of said device; and, said arrangement further comprising optical means interposed between said device and said radiation source for transmitting said radiation into said space.

10. The arrangement of claim 1, said mounting means being a glass plate having a supporting surface for supporting the specimen; and, said supporting surface being configured as a diffusing screen.

11. The arrangement of claim 1, said radiation-integrating device being an Ulbricht sphere.

12. The arrangement of claim 1, said radiation-integrating device being of generally cylindrical shape.

13. The arrangement of claim 1, said wall having an opening formed therein to permit the diffused radiation to pass out of said space; and, said arrangement further comprising a cylindrically-shaped tube having an inner wall reflective surface defining an interior space; said tube defining seating means for receiving said device thereon so as to cause said opening to communicate with said interior space of said tube; and, said mounting means being disposed with respect to the tube so as to cause said specimen to be disposed within said interior space of said tube.

14. The arrangement of claim 1, said specimen being a precious stone.

* * * * *